(12) United States Patent
Hashido et al.

(10) Patent No.: US 9,072,443 B2
(45) Date of Patent: Jul. 7, 2015

(54) ENDOSCOPE HOOD AND ENDOSCOPE WITH THE SAME MOUNTED THEREON

(75) Inventors: Hiroaki Hashido, Akita (JP); Etsuro Yamabe, Akita (JP); Shinetsu Harata, Akita (JP)

(73) Assignee: SUMITOMO BAKELITE CO., LTD., Tokyo (JP)

( * ) Notice: Subject to any disclaimer, the term of this patent is extended or adjusted under 35 U.S.C. 154(b) by 151 days.

(21) Appl. No.: 13/259,952

(22) PCT Filed: Apr. 8, 2010

(86) PCT No.: PCT/JP2010/002570
§ 371 (c)(1),
(2), (4) Date: Sep. 23, 2011

(87) PCT Pub. No.: WO2010/116745
PCT Pub. Date: Oct. 14, 2010

(65) Prior Publication Data
US 2012/0071724 A1    Mar. 22, 2012

(30) Foreign Application Priority Data

Apr. 10, 2009   (JP) .................... 2009-095467

(51) Int. Cl.
*A61B 1/04* (2006.01)
*A61B 1/00* (2006.01)

(52) U.S. Cl.
CPC .............. *A61B 1/042* (2013.01); *A61B 1/00089* (2013.01); *A61B 1/00101* (2013.01)

(58) Field of Classification Search
CPC ........... A61B 1/00089; A61B 1/00101; A61B 1/00137
USPC .................... 600/114, 121–123, 127, 129
See application file for complete search history.

(56) References Cited

U.S. PATENT DOCUMENTS 4,726,355 A * 2/1988 Okada .......................... 600/114
5,897,487 A   4/1999 Ouchi
(Continued)

FOREIGN PATENT DOCUMENTS

JP   48-005268 Y   2/1973
JP   10-323323 A   12/1998
(Continued)

OTHER PUBLICATIONS

Extended European Search Report dated Jul. 30, 2012, issued in corresponding European patent application No. 10761449.7.
(Continued)

*Primary Examiner* — Thomas J Sweet
*Assistant Examiner* — Kevin G Barry, III
(74) *Attorney, Agent, or Firm* — Westerman, Hattori, Daniels & Adrian, LLP

(57) ABSTRACT

An endoscope hood (1) has a cylindrical shape with both ends opened and is mounted on a tip end portion (3) in a longitudinal axis direction of an endoscope (2) provided with an optical system at least including an observation system (5) and a treatment system to be used. The endoscope hood (1) is provided with an endoscope mounting unit (18) having a base end side opening (21) configured to be mounted on the tip end portion (3) of the endoscope (2) and a hood main body (17) having a tip end side opening (10) of which outer diameter perpendicular to the longitudinal axis direction is smaller than the outer diameter of the base end side opening (21), wherein, in a state in which the base end side opening (21) is mounted on the tip end portion (3) and the tip end portion (3) is seen in the longitudinal axis direction, the optical system and the treatment system are located on the inside of the tip end side opening (10).

10 Claims, 8 Drawing Sheets

(56) References Cited

U.S. PATENT DOCUMENTS

| | | | |
|---|---|---|---|
| 6,086,583 A * | 7/2000 | Ouchi | 606/41 |
| 8,480,657 B2 * | 7/2013 | Bakos | 600/114 |
| 2003/0216613 A1 * | 11/2003 | Suzuki et al. | 600/104 |
| 2005/0043584 A1 * | 2/2005 | Nozue | 600/127 |
| 2006/0020264 A1 * | 1/2006 | Crowley et al. | 606/41 |
| 2006/0111614 A1 * | 5/2006 | Saadat et al. | 600/129 |
| 2008/0058586 A1 | 3/2008 | Karpiel | |
| 2009/0105539 A1 * | 4/2009 | Skerven et al. | 600/114 |
| 2009/0112062 A1 * | 4/2009 | Bakos | 600/114 |

FOREIGN PATENT DOCUMENTS

| | | | |
|---|---|---|---|
| JP | 11-104063 A | 4/1999 |
| JP | 2001-149313 A | 6/2001 |
| JP | 2002-330918 A | 11/2002 |
| JP | 2003-230531 A | 8/2003 |
| JP | 2005-080866 A | 3/2005 |
| JP | 2006-325867 A | 12/2006 |
| JP | 2008-206559 A | 9/2008 |

OTHER PUBLICATIONS

International Search Report of PCT/JP2010/002570, mailing date May 11, 2010.

Japanese Office Action dated Feb. 4, 2014, issued in corresponding Japanese application No. 2011-508251 (2 pages).

* cited by examiner

ENDOSCOPE HOOD AND ENDOSCOPE WITH THE SAME MOUNTED THEREON

TECHNICAL FIELD

The present invention relates to an endoscope hood and an endoscope on which the endoscope hood is mounted.

BACKGROUND ART

Progress in an endoscopic examination has enabled detection of a mucosa tumor in a lumen such as a digestive tract. A great number of mucosal resections have been carried out to ablate a mucosa tissue from a muscle tissue under a mucosa to remove the mucosa tissue endoscopically using a treatment tool such as a diathermy knife. Yet, if an endoscopic submucosal resection is carried out to peel and resect the mucosa of a wide area at once, a problem occurs in the resection when the mucosa peeled and ablated covers a site to be ablated from a muscle layer. Blind ablation is necessary in this case, thus increasing risk of occurrence of perforation of the digestive tract and the like if the treatment tool such as the diathermy knife injures the muscle layer.

Efficient ablation of the mucosa in the wide area requires that the diathermy knife and the like be put on a boundary between the mucosa and the muscle layer while tensile force is applied in a direction in which the ablated mucosa peels from the muscle layer. Nevertheless, many endoscopes are provided with only one forceps aperture for allowing the treatment tool such as the diathermy knife to pass. The forceps aperture of the endoscope has thus no space for allowing the size larger than that of the diathermy knife and the like to pass. As a result, a problem exists where grasping forceps and the like are unavailable to apply the tensile force to a living tissue such as the mucosa.

Disclosed is an endoscope hood configured to be mounted on a tip end of the endoscope, the endoscope hood aiming to prevent the blind ablation described above in the endoscopic submucosal resection and the like (See Patent Document 1, for example). The endoscope hood has the tip end provided with a projection so as to ensure a predetermined distance between the tip end of the endoscope (object lens) and a treatment site. The treatment site is thus observable in an excellent manner. Still, a problem exists where the endoscope hood has difficulty in getting between the mucosa and the muscle layer, because the endoscope hood itself has a straight-cylindrical shape in a longitudinal axis direction. Accordingly, a problem exits where it is difficult to apply the tensile force for peeling the ablated mucosa from the muscle layer.

Also disclosed is the endoscope hood tapering off toward the tip end side (See Patent Document 2, for example). In the endoscope hood, the object lens on the tip end of the endoscope is arranged eccentrically with respect to a central axis of the endoscope. That is to say, a tip end side opening of the endoscope hood has a central axis formed eccentrically so that the central axis of the tip end side opening substantially conforms to a central axis of the object lens. As a result, a problem exists where a linear route cannot be secured from a treatment tool outlet port on the tip end of the endoscope to the treatment site, and operability of the treatment tool such as the diathermy knife deteriorates.

RELATED DOCUMENT

Patent Document

[Patent Document 1] Japanese Patent Application Laid-Open No. 2003-230531

[Patent Document 2] Japanese Patent Application Laid-Open No. 2006-325867

DISCLOSURE OF THE INVENTION

Problem to be Solved by the Invention

An object of the present invention is to provide the endoscope hood capable of easily assist mucosal dissection and the like while ensuring an excellent endoscope eyesight and obtaining excellent operability of the treatment tool such as the diathermy knife in the endoscopic submucosal resection and the like, and the endoscope on which the endoscope hood is mounted.

Means for Solving the Problem

Such object is achieved by the present invention described in following (1) to (11).

(1) A cylindrical endoscope hood having both ends open, the endoscope hood being used by mounting on a tip end portion in a longitudinal axis direction of the endoscope, the endoscope including an optical system including at least an observation optical system and a treatment system, the endoscope hood including: an endoscope mounting unit having a base end side opening which is configured to be mounted on the tip end portion of the endoscope; and a hood main body having a tip end side opening which has outer diameter smaller than that of the base end side opening, the outer diameter of the tip end side opening being perpendicular to the longitudinal axis direction of the endoscope, wherein the base end side opening is mounted on the tip end portion of the endoscope so that the optical system and the treatment system are located on the inside of the tip end side opening when the tip end portion of the endoscope is viewed in the longitudinal axis direction of the endoscope.

(2) The endoscope hood according to (1), wherein a cross section in the longitudinal axis direction of the hood main body has ridge lines, at least one of the ridge lines including a tapered portion tapering off toward the tip end side opening.

(3) The endoscope hood according to (2), wherein the cross section in the longitudinal axis direction has a ridge line, the ridge line including a linear portion which is substantially parallel to a central axis of the endoscope, the linear portion being opposite to the tapered portion of the hood main body.

(4) The endoscope hood according to (2) or (3), wherein the tapered portion has an outer surface inclination angle equal to or more than 5 degrees and equal to or less than 30 degrees.

(5) The endoscope hood according to any one of (2) to (4), wherein the tapered portion has an inner surface inclination angle equal to or more than 3 degrees and equal to or less than 20 degrees.

(6) The endoscope hood according to any one of (1) to (5), wherein the tip end side opening of the hood main body has at least one inclined portion at an angle equal to or more than 5 degrees and equal to or less than 30 degrees with respect to a direction perpendicular to a longitudinal axis.

(7) The endoscope hood according to any one of (1) to (6), wherein at least one substantially oval drain hole is formed in a vicinity of a base end portion of the hood main body, the substantially oval drain hole being formed to have large size in a circumferential direction.

(8) The endoscope hood according to (7), wherein the drain hole has an area equal to or more than 3 square millimeters and equal to or less than 15 square millimeters.

(9) The endoscope hood according to any one of (1) to (8), wherein at least an inner surface of the hood main body is subjected to hydrophilic treatment.

(10) An endoscope including an optical system at least including an observation optical system and a treatment system, the endoscope having a tip end portion in a longitudinal axis direction, the tip end portion being mounted on a cylindrical endoscope hood having both ends open, wherein the endoscope hood includes an endoscope mounting unit having a base end side opening which is configured to be mounted on the tip end portion of the endoscope; and a hood main body having a tip end side opening which has outer diameter smaller than an outer diameter of the base end side opening, the outer diameter being perpendicular to the longitudinal axis direction, and wherein when the tip end portion of the endoscope is viewed in the longitudinal axis direction, the optical system and the treatment system are located on the inside of the tip end side opening.

(11) The endoscope according to (10), wherein the hood main body has a tapered shape tapering off from the endoscope mounting unit toward the tip end side opening, and when the tip end portion of the endoscope is viewed in the longitudinal axis direction, the observation optical system has a central axis in the longitudinal axis direction, the central axis being arranged at an angle equal to or more than 30 degrees and equal to or less than 60 degrees or equal to or more than −60 degrees and equal to or less than −30 degrees around a center of the base end side opening with respect to an axis passing through an innermost position of the tip end side opening and the center.

Effect of the Invention

According to the present invention, provided are the endoscope hood capable of easily assist the mucosal dissection and the like while ensuring the excellent endoscope eyesight in the endoscopic submucosal resection and the like, and the endoscope on which the endoscope hood is mounted may be provided.

BRIEF DESCRIPTION OF THE DRAWINGS

The above-described object, another object, characteristics and advantages are further clarified by preferred embodiments to be described hereinafter and following drawings associated with the same.

DESCRIPTION OF EMBODIMENTS

Figure 1:
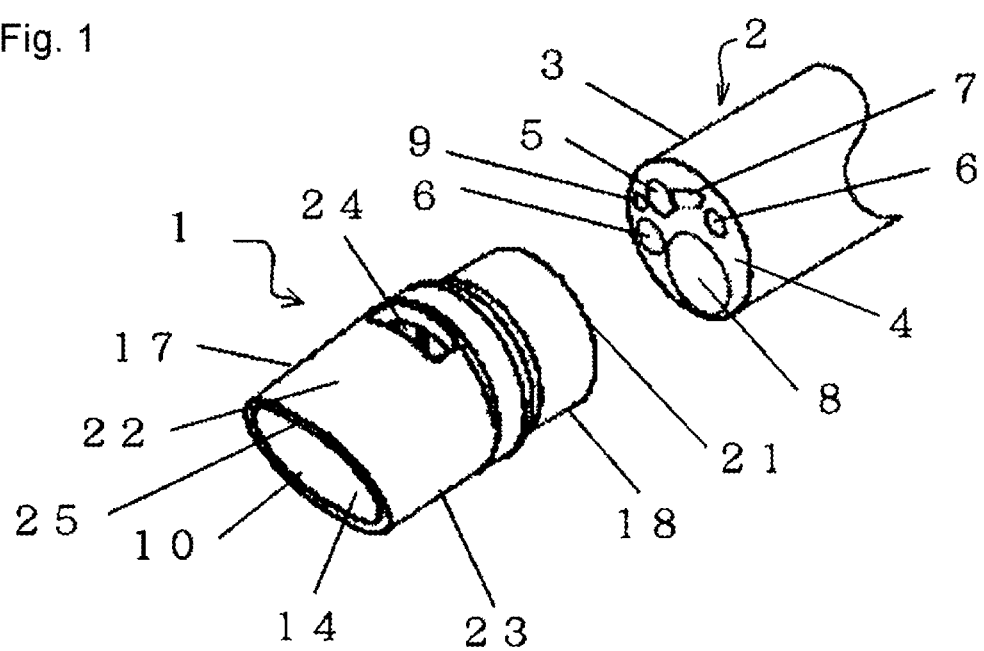
FIG. 1 is a perspective view illustrating an endoscope hood and a tip end portion of an endoscope of a first embodiment of the present invention.

An endoscope hood of this embodiment is hereinafter described in detail with reference to the drawings. Meanwhile, in the description of the drawings, a same reference numeral is assigned to same components and the description will not be repeated.

Figure 2:
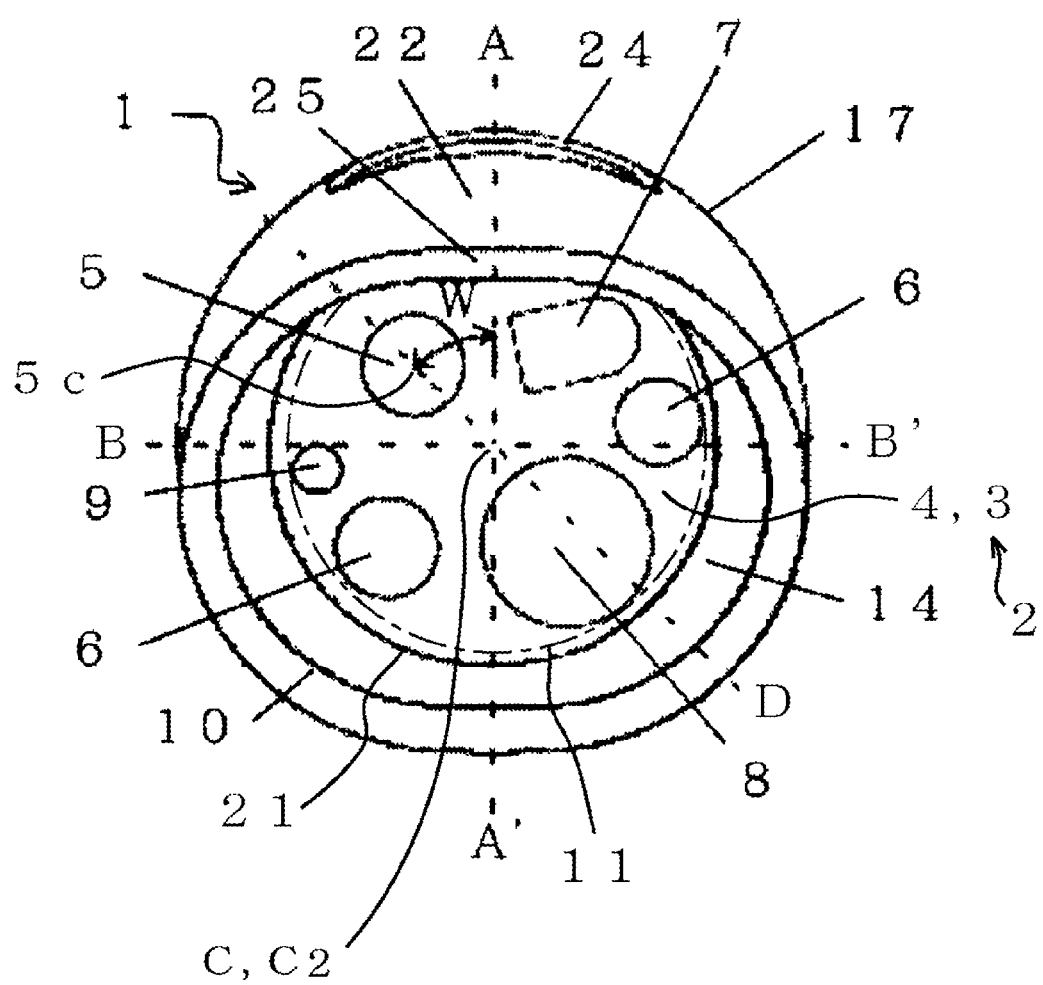
FIG. 2 is an enlarged front view of the hood in FIG. 1, the hood being mounted on the tip end portion of the endoscope, the hood being viewed from an opening side of the hood.
Figure 3:
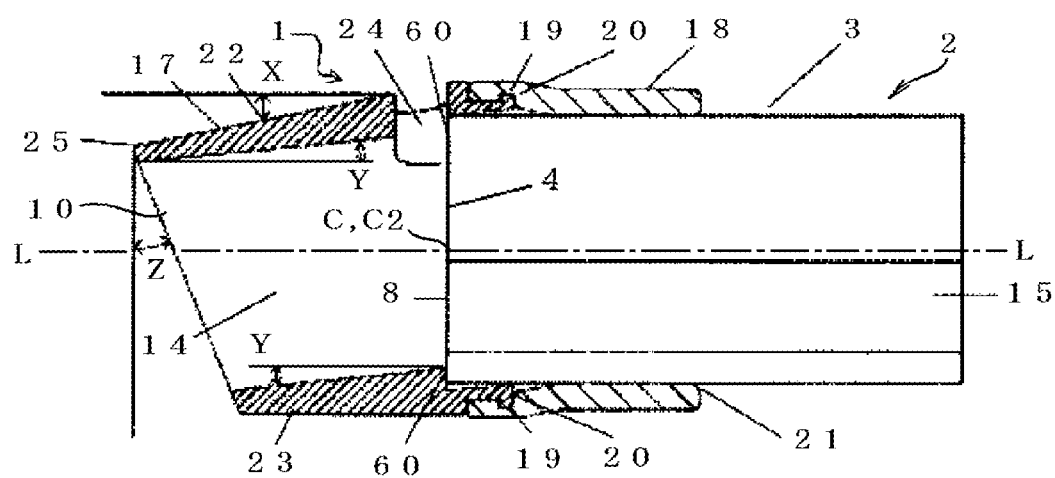
FIG. 3 is a longitudinal sectional view along a line A-A' in FIG. 2.

FIG. 1 is a perspective view of an endoscope hood 1 (hereinafter, sometimes simply referred to as a "hood") and a tip end portion 3 of an endoscope 2 of a first embodiment of the present invention, the hood 1 being to be mounted on the endoscope 2. FIG. 2 is an enlarged front view of the hood 1, the hood 1 being mounted on the tip end portion 3 of the endoscope 2, the hood 1 being viewed from an opening side of the hood 1 and FIG. 3 is a longitudinal sectional view of the hood 1 cut in a longitudinal axis direction along a line A-A' of FIG. 2. The longitudinal axis direction of the hood 1 in this embodiment is intended to mean the longitudinal axis direction of the endoscope 2. Dimensions in the longitudinal axis direction and in a radial direction of the hood 1 are arbitrary. A longitudinal section of the hood 1 is intended to mean a cross section of the hood 1 cut in the longitudinal axis direction.

The endoscope 2 has a tip end which is provided with a hard tip end portion 3. The endoscope 2 has a base end side (not illustrated) which is provided with an operating unit (not illustrated). If the operating unit is operated, a curved portion (not illustrated), which connects with the tip end portion 3, is operated to bend so that a direction of the tip end portion 3 changes.

The tip end portion 3 of the endoscope 2 has an end face 4 which is provided with an observation optical system 5, an illumination optical system 6, an air-supply/water-supply nozzle 7, a treatment tool outlet port 8, and an injection hole 9, the observation optical system 5 and the illumination optical system 6 each being optical system, the treatment tool outlet port 8 being a treatment system. Hereinafter, the observation optical system 5, the illumination optical system 6, the air-supply/water-supply nozzle 7, the treatment tool outlet port 8, and the injection hole 9 are collectively referred to as "functional components".

The observation optical system 5 is configured to observe an object. In the observation optical system 5, object light is converted to an electrical signal by a charge coupled device (CCD) provided on a light path of the object light, and the converted electrical signal is transmitted through a signal cable to be displayed as an image.

A light guide (not illustrated) is arranged in the illumination optical system 6 and the light guide connects with a light source switch (not illustrated) of an endoscope main body (not illustrated). If the light source switch is pressed in order that the light guide emits light, illumination light is radiated to a tip end side in front of the illumination optical system 6.

The air-supply/water-supply nozzle 7 is arranged from the tip end portion 3 of the endoscope 2 to the operating unit of the endoscope main body such that gas such as air and liquid such as water is injected by operation of the operating unit. The injection of the gas and the liquid from the air-supply/water-supply nozzle 7 can remove a stain adhered to the tip end portion 3 and the observation optical system 5 of the endoscope 2 and to an inner surface 14 of a hood main body 17.

As illustrated in FIG. 3, a treatment tool insertion path 15 is arranged from the treatment tool outlet port 8 to a treatment tool inlet port (not illustrated) of the operating unit of the endoscope main body so as to penetrate through the tip end portion 3. As a result, a treatment tool 16 such as a diathermy knife can be inserted from the treatment tool inlet port and taken out of the treatment tool outlet port 8 so that treatment is performed on a site of lesion 40 (See FIGS. 4A and 4B). The treatment tool outlet port 8 is arranged so as to connect with an aspiration mechanism of the operating unit of the endoscope main body. Accordingly, rinse water, body fluid and the like can be aspirated through the treatment tool outlet port 8 if the operating unit of the endoscope main body is operated.

The injection hole 9 is arranged from the tip end portion 3 of the endoscope 2 to an injected matter supply port (not illustrated) on the base end side of the endoscope main body. If the injected matter supply port connects with a water-supplying device (not illustrated), the liquid such as the water can be injected forward from the injection hole 9.

The hood 1 of this embodiment illustrated in FIG. 1 is used by mounting on the tip end portion 3 in the longitudinal axis direction of the endoscope 2 provided with the optical system, which includes at least the observation optical system 5, and the treatment system (treatment tool outlet port 8). The hood 1 has a cylindrical shape with both ends open. The hood 1 may have a straight-pipe shape or may have a curved-pipe shape slightly curved or bent.

The hood 1 is provided with an endoscope mounting unit 18 having a base end side opening 21 which is configured to be mounted on the tip end portion 3 of the endoscope 2, and a hood main body 17 having a tip end side opening 10 which has outer diameter smaller than the outer diameter of the base end side opening 21, the outer diameter of the tip end side opening 10 being perpendicular to the longitudinal axis direction of the endoscope 2.

The endoscope mounting unit 18 is formed of an elastic material such as rubber and polyvinyl chloride to have a substantially cylindrical shape, for example. As illustrated in FIG. 3, an annular concave portion 19 is preferably formed in a circumferential direction on an inner periphery on the tip end side of the endoscope mounting unit 18.

The concave portion 19 engages with a convex portion 20 annularly formed on an outer periphery on the base end side of the hood main body 17.

Accordingly, the base end portion of the hood main body 17 and the tip end portion of the endoscope mounting unit 18 separately formed can be surely fixed to each other.

Meanwhile, although the hood main body 17 and the endoscope mounting unit 18 may be engaged with each other by fitting as illustrated in FIG. 3, they may be fixed to each other by bonding in place of or in conjunction with this.

The hood main body 17 is preferably formed of transparent resin and the like. Although the transparent resin includes polycarbonate, acrylonitrile butadiene styrene, the polyvinyl chloride and the like, for example, the polycarbonate is preferably used for reasons of transparency, chemical resistance, and heat resistance.

If the transparent resin material is used, a lumen medial wall can be observed through the hood 1 by means of the endoscope 2.

A stopper unit 60 may be provided on the base end side of the hood main body 17. The stopper unit 60 of this embodiment is a stepped portion formed on the inner periphery of the base end portion of the hood main body 17. An inner diameter of the stopper unit 60 is smaller than an opening diameter (inner diameter) on the base end side of the hood main body 17.

If the tip end portion 3 of the endoscope 2 is pushed into the hood main body 17 such that the end face 4 of the tip end portion 3 abuts the stopper unit 60, the tip end portion 3 of the endoscope 2 can be surely mounted on the hood main body 17 to fix to the hood main body 17. The inner diameter of the hood main body 17 in the stopper unit 60 is made larger than a diameter of a virtual circular area 11 (See FIG. 2), the virtual circular area 11 enveloping the functional components such as the treatment tool outlet port 8 and the injection hole 9. Accordingly, the functional components such as the treatment tool outlet port 8 and the injection hole 9 on the end face 4 of the endoscope 2 do not interfere with the stopper unit 60.

As illustrated in FIG. 2, in the hood 1 of this embodiment, the base end side opening 21 is mounted on the tip end portion 3 of the endoscope 2 so that the observation optical system 5, the illumination optical system 6 (optical system), and the treatment tool outlet port 8 (treatment system) are located on the inside of the tip end side opening 10 when the tip end portion 3 of the endoscope 2 is viewed from the tip end side in the longitudinal axis direction of the endoscope 2 (hereinafter, sometimes referred to as forward view).

Accordingly, an excellent endoscope eyesight can be ensured and it is possible to improve operability of the treatment tool 16 such as the diathermy knife.

That is to say, presence of the hood 1 is not a forward obstacle in the longitudinal axis direction of the observation optical system 5, the illumination optical system 6, and the treatment tool outlet port 8, so that the excellent eyesight of the endoscope 2 can be ensured. A linear portion can be secured from the treatment tool outlet port 8 to a site of treatment, so that the operability of the treatment tool 16 such as the diathermy knife can be made excellent.

The fact that the functional components of the endoscope 2 are located on the inside of the tip end side opening 10 is herein intended to mean that a center position of each component, which composes the optical system or the treatment system, is located on the inside of the tip end side opening 10 in the forward view. It is more preferable that each entire functional component is fully located on the inside of the tip end side opening 10 in the forward view. Nevertheless, unless each function of the optical system and the treatment system is substantially lost, a partial area of the components may be located behind the inner surface 14 of the hood main body 17 in the forward view and may be not exposed to the inside of the tip end side opening 10.

When the optical system is composed of a plurality of components, the fact that the optical system is located on the inside of the tip end side opening 10 in the forward view is intended to mean that at least one of the components, which compose the optical system, is located on the inside of the tip end side opening 10 in the forward view. It is more preferable that all the components, which compose the optical system, are located on the inside of the tip end side opening 10 in the forward view.

The treatment system is similar to the optical system, and when the treatment system is composed of a plurality of components, the fact that the treatment system is located on the inside of the tip end side opening 10 in the forward view is intended to mean that at least one of the components, which compose the treatment system, is located on the inside of the tip end side opening 10 in the forward view. It is more preferable that all the components, which compose the treatment system, are located on the inside of the tip end side opening 10 in the forward view.

It is preferable the cross section of the hood main body 17 has ridge lines in the longitudinal axis direction, at least one of the ridges being formed as a tapered portion 22 tapering off from the endoscope mounting unit 18 toward the tip end side opening 10.

Such a shape allows the outer diameter of the tip end side opening 10 perpendicular to the longitudinal axis direction of the hood main body 17 to be smaller than the outer diameter of the base end side opening 21 of the endoscope mounting unit 18. The hood main body 17 thus easily gets between a mucosa 41 and a muscle layer 43, and tensile force is easily applied for peeling the incised mucosa 41 from the muscle layer 43 (See FIG. 4B).

That is to say, in the hood 1 of this embodiment, the diameter in the direction perpendicular to the longitudinal axis of the tip end side opening 10 is smaller than that of the base end side opening 21. The diameters in the direction perpendicular to the longitudinal axis of the tip end side opening 10 and the base end side opening 21 are the diameters relating to projected shapes of the openings in the longitudinal axis direction. When the projected shape is not circular, the outer diameter in the direction perpendicular to the longitudinal axis of the opening is intended to mean a short diameter of the projected shape (that is to say, the diameter of an inscribed circle of the projected shape). When opening directions (normal directions of the openings) of the tip end side opening 10 and the base end side opening 21 do not conform to the longitudinal axis direction, the diameters in the direction perpendicular to the longitudinal axis of the openings do not necessarily conform to the opening diameter seen from the front of the opening. The diameter in the direction perpendicular to the longitudinal axis is thus distinguished from the opening diameter as described above. A size of the opening diameters of the tip end side opening 10 and the base end side opening 21 are arbitrary.

When the diameter in the direction perpendicular to the longitudinal axis of the tip end side opening 10 is made smaller than that of the base end side opening 21, the hood main body 17 easily gets between a mucosa 41 and a muscle layer 43.

It is preferable that the cross section has a ridge line in the longitudinal axis direction, the ridge line having a linear portion 23 substantially parallel to a central axis of the endoscope 2, the linear portion 23 being opposite to the tapered portion 22 of the hood main body 17. Accordingly, when the treatment tool 16 such as the diathermy knife is projected from an outlet port of the treatment tool insertion path 15 (treatment tool outlet port 8), the treatment can be performed without interference with the inner surface 14 of the hood main body 17. Also, at the time of the treatment, the linear portion 23 can hold a submucosa 42. That is to say, since the linear portion 23 of the hood main body 17 is formed in alignment with the endoscope mounting unit 18 circumferentially attached to the tip end portion 3 of the endoscope 2, the linear portion 23 does not bite into the submucosa 42 and the linear portion 23 can hold the submucosa 42.

As illustrated in FIG. 2, a shape of the tip end side opening 10 may be an oval or an ellipse.

As illustrated in FIG. 3, an outer surface inclination angle X of the tapered portion 22 of the hood main body 17 is preferably equal to or more than 5 degrees and equal to or less than 30 degrees. The outer surface inclination angle X is herein a maximum value of an angle between an outer surface of the hood main body 17 and the longitudinal axis. In other words, the outer surface inclination angle X is an angle between a maximum gradient of the tapered portion 22 and the longitudinal axis.

The outer surface inclination angle X is more preferably equal to or more than 10 degrees and equal to or less than 20 degrees. If a range of the outer surface inclination angle X of the tapered portion 22 sets as described above, the hood main body 17 easily gets between the mucosa 41 and the muscle layer 43, so that the excellent eyesight can be secured on the endoscope 2. Further, the water can be injected from the injection hole 9 to a target site without injection of the water to the inner surface 14 of the hood main body 17.

It is preferable that an inner surface inclination angle Y of the tapered portion 22 of the hood main body 17 is equal to or more than 3 degrees and equal to or less than 20 degrees. This is more preferably equal to or more than 5 degrees and equal to or less than 15 degrees. The inner surface inclination angle Y is smaller than the outer surface inclination angle X. If a range of the inner surface inclination angle Y of the tapered portion 22 sets as described above, more excellent eyesight of the endoscope 2 can be obtained.

In the hood 1 of this embodiment, as illustrated in FIG. 3, the inner surface inclination angle Y of the tapered portion 22 is equal to the inner surface inclination angle Y of the linear portion 23. That is to say, the inner surface 14 of the hood main body 17 has the straight-pipe shape which is inclined with respect to the longitudinal axis at the inner surface inclination angle Y.

Figure 4A:
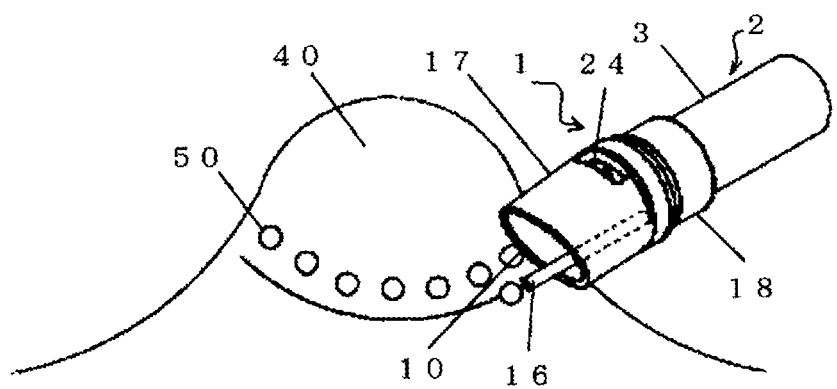
FIG. 4A and FIG. 4B are illustrative diagrams illustrating a treatment method.
Figure 4B:
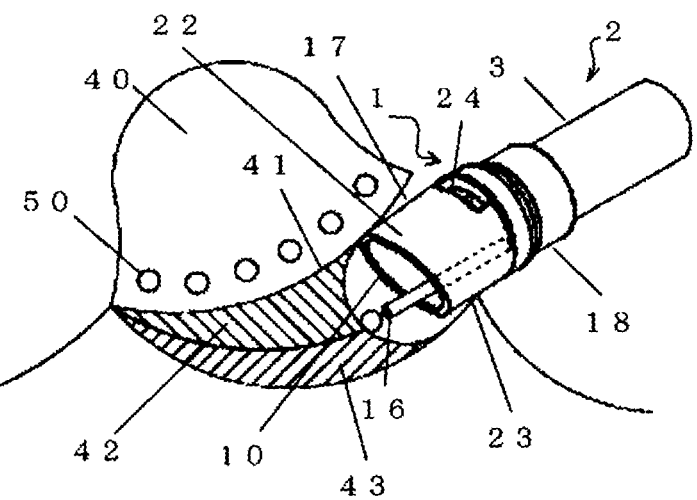

The hood main body 17 of this embodiment is formed such that the tapered portion 22 projects from the linear portion 23 toward the tip end side in the longitudinal axis direction. As illustrated in FIG. 3, the tip end side opening 10 of the hood main body 17 is such that an angle Z with respect to the direction perpendicular to the longitudinal axis is preferably equal to or more than 5 degrees and equal to or less than 30 degrees. This is more preferably equal to or more than 10 degrees and equal to or less than 25 degrees. The angle of the above-described range as illustrated in FIG. 4B allows the tip end side opening 10 of the hood 1 to be in close contact with the site of lesion 40, the mucosa 41, and the submucosa 42, the lesion 40 having a shape being smoothly raised in particular. Procedure can be thus easily performed.

It is preferable that there is at least one inclined portion at the angle Z with respect to the direction perpendicular to the longitudinal axis. When there is a plurality of inclined portions, an entire surface of the hood main body 17 can easily get into the mucosa 41 and hold the submucosa 42, while the above-described effect is achieved.

Figure 5:
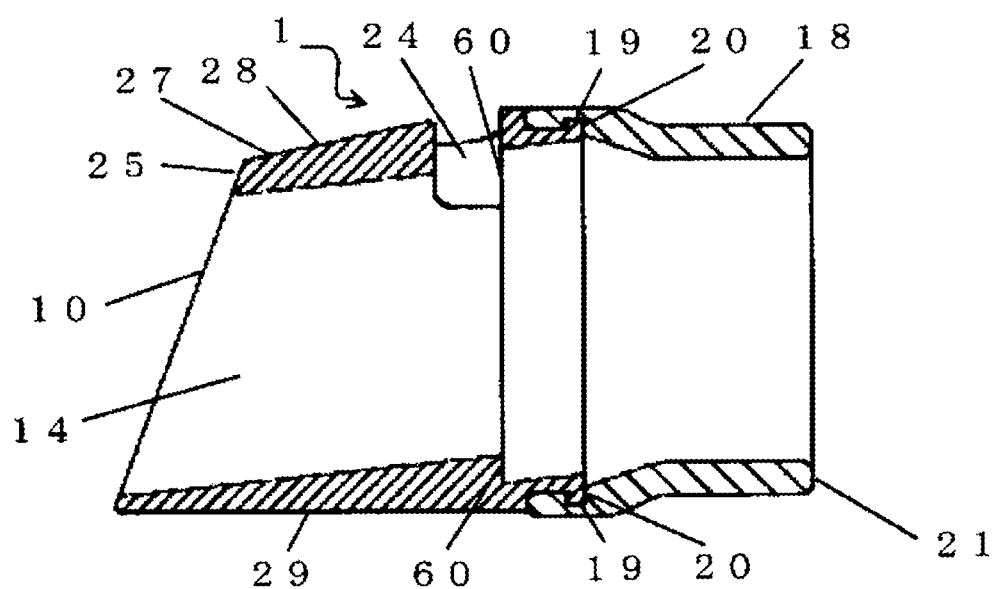
FIG. 5 is a longitudinal sectional view of the endoscope hood of a second embodiment of the present invention.

A second embodiment of the hood 1 of the present invention is illustrated in FIG. 5. This is different from the first embodiment (FIG. 3) in that a tapered portion 28 of a hood main body 27 is shorter than a linear portion 29. Accordingly, also when the endoscope 2 is rotated by 180 degrees depending on a position of the site of lesion 40 so that the treatment is performed, the hood main body 27 easily gets into a gap between the mucosa 41 and the muscle layer 43. Also, since the linear portion 29 becomes long, the submucosa 42 can be held more strongly.

Figure 6:
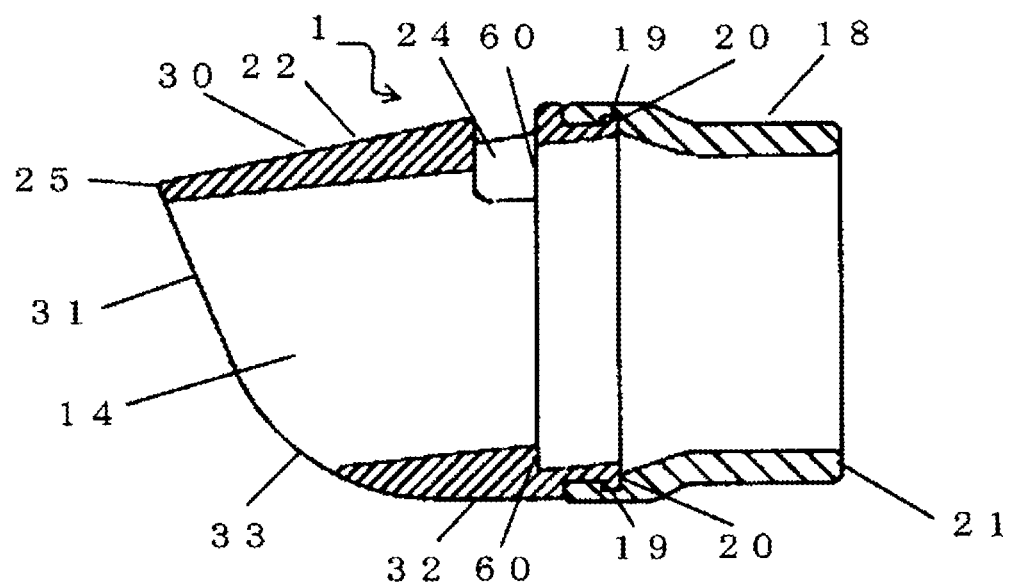
FIG. 6 is a longitudinal sectional view of the endoscope hood of a third embodiment of the present invention.

A third embodiment of the hood 1 of the present invention is illustrated in FIG. 6. This is different from the first embodiment (FIG. 3) in that a contact point between the linear portion 32 and the tip end side opening 31 is a large circular arc portion 33 when a tip end side opening 31 of a hood main body 30 is seen from a side surface. Accordingly, the eyesight of the endoscope 2 further improves and the endoscope 2 can easily get into the mucosa 41.

The side surface of the hood 1 is intended to mean the surface in a direction normal to a plane between a direction of inclination of the tip end side opening 31 and the longitudinal axis direction (See FIGS. 3, 5, 6, and 7).

Figure 7:
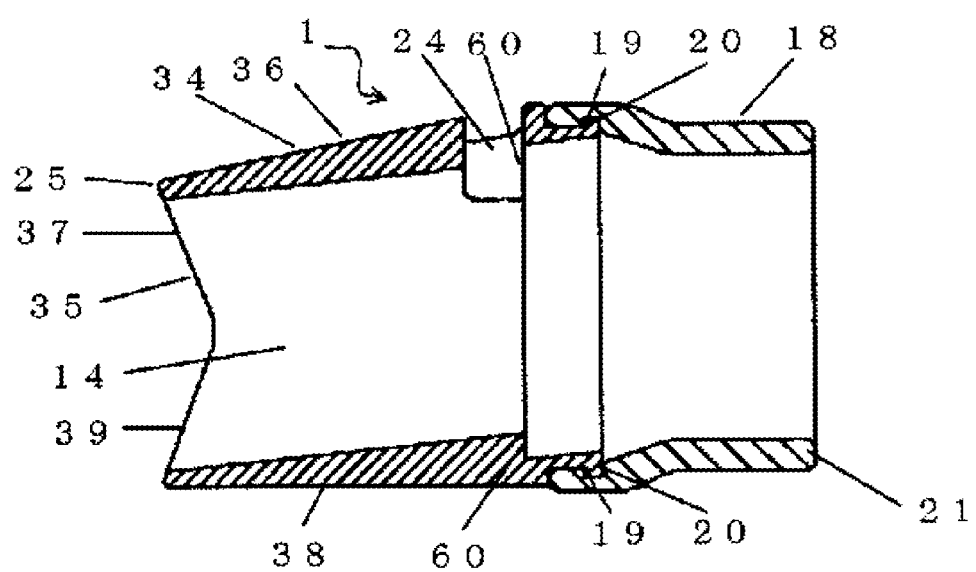
FIG. 7 is a longitudinal sectional view of the endoscope hood of a fourth embodiment of the present invention.

A fourth embodiment of the hood 1 of the present invention is illustrated in FIG. 7. This is different from the first embodiment (FIG. 3) in having a plurality of inclined portions 37 and 39 perpendicular to each other. More specifically, when the tip end side opening 35 of the hood main body 34 is seen from the side surface, the inclined portion 37 falling from a tapered portion 36 of the hood main body 34 intersects with an inclined portion 39 rising from a linear portion 38. Accordingly, an entire hood main body 34 can easily get into the mucosa 41 and hold the submucosa 42 (See FIG. 4B).

The inclined portions 37 and 39 of this embodiment are inclined in a retreat direction from each tip end of the tapered portion 36 and the linear portion 38 toward the base end side (rightward in the drawing). In other words, an extreme tip end position of the hood main body 34 is a falling position of the inclined portion 37 or a rising position of the inclined portion 39. An intersection of the inclined portions 37 and 39 is located on a side closer to the base end.

Figure 8:
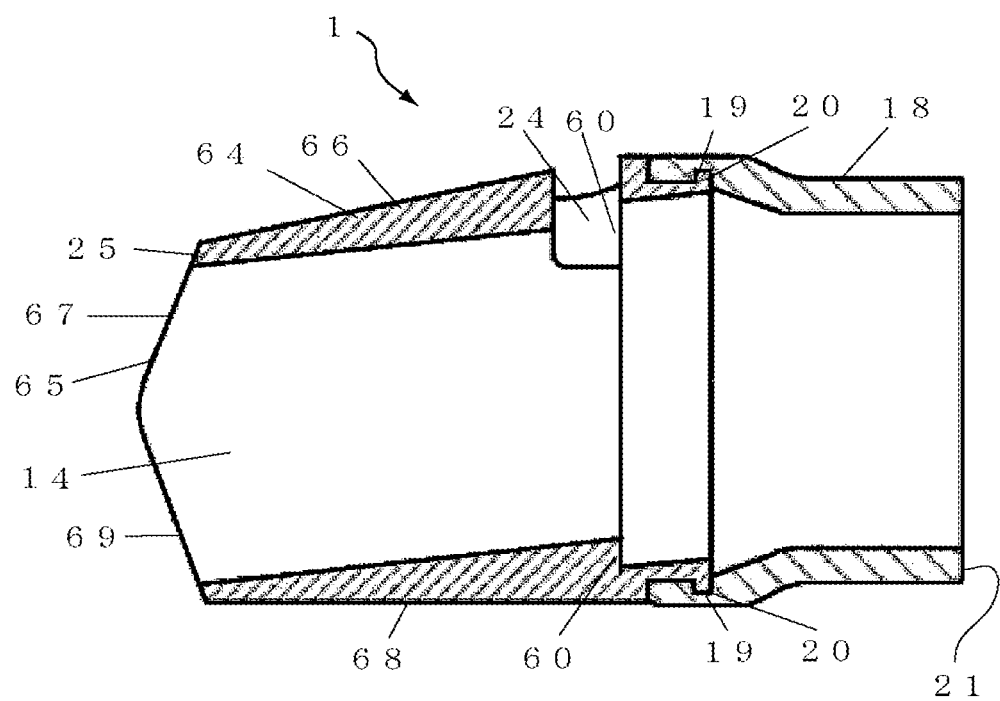
FIG. 8 is a longitudinal sectional view of the endoscope hood of a fifth embodiment of the present invention.

A fifth embodiment of the hood 1 of the present invention is illustrated in FIG. 8. This is different from the fourth embodiment (FIG. 7) in that the directions of inclination of the inclined portions 67 and 69 are inverted. More specifically, when a tip end side opening 65 of a hood main body 64 is seen from the side surface, the inclined portion 67 falls from a taper tip end portion 25 of a tapered portion 66 in a direction to project toward the tip end side of the hood main body 64 (leftward in the drawing). Also, the inclined portion 69 rises from the tip end of the linear portion 68 in the direction to project toward the tip end side of the hood main body 64. Accordingly, the intersection of the inclined portions 67 and 69 becomes the extreme tip end position of the hood main body 64.

According to the hood 1 of this embodiment, an entire hood main body 64 can easily get into the mucosa 41 and hold the submucosa 42 (See FIG. 4B) and the mucosa 41 and the submucosa 42, being in front of the hood 1, can be surely held.

Also, it is preferable that at least one drain hole 24 formed to have large size in the circumferential direction is formed in the vicinity of the base end portion of the hood main body 17 (See FIGS. 1, 2, 3, 5, 6, 7, and 8). The drain hole 24 thus formed allows the water, the body fluid and the like entering the inner surface 14 of the hood main body 17 to remove even in a state in which the treatment tool 16 such as the diathermy knife is inserted to the treatment tool outlet port 8. If the drain hole 24 is provided in the vicinity of the base end portion of the hood main body 17, the drain hole 24 is out of the eyesight of the endoscope 2 and the excellent eyesight of the endoscope 2 can be maintained at the time of the treatment.

The drain hole 24 of this embodiment is a substantial oval of which diameter is small in the longitudinal axis direction and large in the circumferential direction. The substantial oval herein includes the oval, the ellipse, and a rounded corner slit shape. Since a large size direction of the drain hole 24 is in the circumferential direction, an opening area for sufficiently removing the water, the body fluid and the like is available while the interference with the eyesight of the endoscope 2 is prevented. The shape of the drain hole 24 may be a circle in addition to the substantial oval.

A size of the drain hole 24 is preferably equal to or more than 3 square millimeters and equal to or less than 15 square millimeters. This is more preferably equal to or more than 6 square millimeters and equal to or less than 12 square millimeters. If a range of the size of the drain hole 24 sets as described above, the water, the body fluid and the like hardly remains on the inner surface 14 of the hood main body 17.

If the range of the area of the drain hole 24 sets as described above, aspiration can sustain even when the aspiration mechanism of the operating unit of the endoscope main body aspirates the rinse water, the body fluid, and the like through the treatment tool outlet port 8 and even when the site of resected lesion 40 is allowed to be in close contact with the tip end side opening 10 of the hood main body 17 so that the site of the lesion 40 is aspirated.

The drain hole 24 also acts as an air-intake opening for aspiration through the treatment tool outlet port 8. By this function, when the site of lesion 40 is adsorbed to the tip end side opening 10 of the hood main body 17, excessive aspiration is not performed. A working area thus does not narrow in the inner surface 14 of the hood main body 17 even if the site of lesion 40 is aspirated, and the water is so sufficiently aspirated and discharged through the treatment tool outlet port 8 that the eyesight of the endoscope 2 can secured. Since the substantially oval drain hole 24 of which small diameter is in the longitudinal axis direction in the vicinity of the base end portion of the hood main body 17 is provided, the drain hole 24 avoids the mucosa 41 and the drain hole 24 is prevented from being blocked to the mucosa 41.

It is preferable that at least the inner surface 14 of the hood main body 17 is subjected to hydrophilic treatment. Accordingly, a drain effect of the inner surface 14 improves and the water, the body fluid and the like entering the hood main body 17 is easily discharged from the tip end side opening 10 and the drain hole 24, so that the eyesight of the endoscope 2 can be efficiently ensured. Further, since the air can be taken from the drain hole 24, it is possible to discharge the water, the body fluid and the like from the treatment tool outlet port 8 by a synergy effect with the hydrophilic treatment, so that the eyesight of the endoscope 2 can be efficiently ensured. Although the hydrophilic treatment is not especially limited, methods including film formation by a gas phase process such as sputtering and deposition, film formation by a liquid phase process such as dipping coating and spin coating, film formation to apply a chemical as a base of a hydrophilic membrane by cloth, absorbent cotton and the like, and a plasma treatment to hydroxylate a surface and the like may be used, for example.

The endoscope 2 of this embodiment is provided with the optical system at least including the observation optical system 5 and the treatment system (treatment tool outlet port 8). The cylindrical endoscope hood 1 with the both ends open is mounted on the tip end portion 3 in the longitudinal axis direction.

The endoscope hood 1 is provided with the endoscope mounting unit 18 having the base end side opening 21 configured to be mounted on the tip end portion 3 of the endoscope 2 and the hood main bodies 17, 27, 30, 34, and 64 having the tip end side openings 10, 31, 35, and 65 of which outer diameters in the direction perpendicular to the longitudinal axis are smaller than the outer diameter of the base end side opening 21.

When the tip end portion 3 of the endoscope 2 is viewed in the longitudinal axis direction (forward view), the optical system (observation optical system 5 and the illumination optical system 6) and the treatment system (treatment tool outlet port 8) are located on the inside of the tip end side openings 10, 31, 35, and 65.

As illustrated in FIGS. 2 and 3, the hood main body 17 has the tapered shape tapering off from the endoscope mounting unit 18 toward the tip end side opening 10. When the tip end portion 3 of the endoscope 2 is viewed in the longitudinal axis direction, a central axis $5c$ in the longitudinal axis direction of the observation optical system 5 is arranged at an angle equal to or more than 30 degrees and equal to or less than 60 degrees or equal to or more than −60 degrees and equal to or less than −30 degrees around a center C with respect to an axis (A-A' line), which passes through an innermost position of the tip end side opening 10 (taper tip end portion 25 in this embodiment) and the center C of the base end side opening 21.

In FIG. 3, a center line L of the hood 1, which passes through the center C of the base end side opening 21 and is parallel to the longitudinal axis direction of the endoscope 2, is indicated by a dashed line. In this embodiment, the above-described axis (A-A' line in FIG. 2) is a plane (axial plane), which passes through the center line L and the taper tip end portion 25, and this corresponds to FIG. 3. The base end side opening 21 of this embodiment has the straight-pipe shape and both of the center C and a center C2 of the end face 4 of the endoscope 2 are located on the center line L. In the hood main body 17, a distance between the taper tip end portion 25 and the center line L is smaller than the distance between the tip end of the linear portion 23 and the center line L. That is to say, the taper tip end portion 25 is located on the innermost position of the tip end side opening 10.

The hood main body 17 may have the straight-pipe shape or may have the curved-pipe shape. That is to say, the hood main body 17 may have a tapered shape in which a tapered portion 22 is provided on a part of a periphery or an entire periphery of the straight pipe linearly extending in the longitudinal axis direction, the tapered shape having a diameter reducing toward the tip end side. Also, the hood main body 17 may have the tapered shape in which the tapered portion 22 is provided on a part of the periphery or the entire periphery of the curved pipe curved or bent in whole, the tapered shape having a diameter reducing toward the tip end side.

The hood 1 of the first embodiment illustrated in FIG. 2 is provided with the tapered portion 22 on the periphery of the straight-pipe shaped hood main body 17. The taper tip end portion 25 in the hood 1 of this embodiment is thus located on the innermost position most closely to the center C in the forward view.

Nevertheless, a case is not limited to the above if the hood main body 17 is provided with the tapered portion on a part of the periphery of the curved pipe in place of this embodiment. For example, when the tapered portion 22 is provided on the periphery of an inner side of a bending direction of the hood main body 17, an opposed position of the taper tip end portion 25 in the tip end side opening 10 might be the innermost position.

The central axis $5c$ in the longitudinal axis direction of the observation optical system 5 is on the center of the observation optical system 5 on the end face 4 (center of a circumcircle). The observation optical system 5 of this embodiment is a substantial circle and the central axis $5c$ is the center of the observation optical system 5.

Herein, a virtual line, which passes through the center C and is perpendicular to the A-A' line, is indicated as a B-B' line in FIG. 2.

In the endoscope 2 of this embodiment, the central axis $5c$ of the observation optical system 5 is located between the A-A' line and the B-B' line.

An angle W between a virtual line D, which passes through the central axis $5c$ of the observation optical system 5 and the center C of the base end side opening 21, and the A-A' line is equal to or more than 30 degrees and equal to or less than 60 degrees or equal to or more than −60 degrees and equal to or less than −30 degrees. That is to say, in a coordinate system of which original point is the center C and of which reference line (angle 0) is in a direction of the taper tip end portion 25, a preferable position of the central axis $5c$ of the observation optical system 5 is at an angle equal to or more than 30 degrees and equal to or less than 60 degrees or equal to or more than 300 degrees and equal to or less than 330 degrees. In other words, the angle W is preferably equal to or more than ±30 degrees and equal to or less than ±60 degrees. The angle W is more preferably equal to or more than ±40 degrees and equal to or less than ±50 degrees.

If the central axis $5c$ of the observation optical system 5 is arranged at the above-described angle, an image of the hood 1 is out of the eyesight of an endoscope image and the sufficient eyesight can be obtained.

The observation optical system 5 is herein preferably arranged so as to be apart from both of the hood main body 17 and the treatment tool outlet port 8, so that the excellent eyesight can be obtained. On the other hand, the treatment tool outlet port 8 through which the treatment tool 16 such as the diathermy knife is inserted has the diameter larger than that of the observation optical system 5 in general as illustrated in FIG. 2. Accordingly, the treatment tool outlet port 8 with the larger diameter is preferably arranged on a side opposite to the taper tip end portion 25 (below the B-B' line in the drawing), so that both of the optical system and the treatment system are arranged on the inside of the tip end side opening 10 in the forward view. The observation optical system 5 is preferably arranged above the B-B' line in the drawing and on a position rotated from the taper tip end portion 25 by substantially 45 degrees so as to be arranged apart from both of the treatment tool outlet port 8 and the taper tip end portion 25. For this reason, the above-described range of the angle W is preferable.

Next, an example of a treatment method when the hood 1 is mounted on the tip end portion 3 of the endoscope 2 is described with reference to FIGS. 4A and 4B.

The hood 1 is mounted on the tip end portion 3 of the endoscope 2. After the endoscope 2 is orally inserted, the treatment tool such as a needle-like knife (not illustrated) connected to a high-frequency power source is inserted from the treatment tool inlet port of the endoscope 2, and in a state in which the treatment tool projects to the treatment tool outlet port 8, circular marking 50 is applied at substantially regular intervals on an entire circumference of the site of lesion 40 while a tip end of the treatment tool such as the needle-like knife is energized with a high-frequency current. Next, the site of lesion 40 bulges by local injection using normal saline solution, hyaluronate sodium and the like. Thereafter, as illustrated in FIG. 4A, the treatment tool 16 such as the diathermy knife connected to the high-frequency power supply is inserted from the treatment tool inlet port of the endoscope 2 and in a state in which the treatment tool 16 projects from the treatment tool outlet port 8, peripheral incision of the site of lesion 40 is made along the marking 50 while the treatment tool 16 such as the diathermy knife is energized with the high-frequency current. At that time, since the eyesight of the endoscope 2 is sufficiently ensured by means of the hood main body 17, it is possible to surely make the peripheral incision of the site of lesion 40 while a state of the lesion 40 is confirmed.

After the peripheral incision of the site of lesion 40 finishes, as illustrated in FIG. 4B, the hood main body 17 is allowed to get into the gap between the mucosa 41 and the muscle layer 43 and the submucosa 42 is peeled while the treatment tool 16 such as the diathermy knife is energized with the high-frequency current. At that time, since the eyesight of the endoscope 2 is sufficiently ensured by means of the hood main body 17, it is possible to surely peel the submucosa 42 while the state of the site of lesion 40 is confirmed.

Since the diameter of the hood main body 17 reduces toward the tip end side by the tapered portion 22, it becomes possible to allow the hood main body 17 to easily get into the gap between the mucosa 41 and the muscle layer 43, and the tensile force for peeling the incised mucosa 41 from the muscle layer 43 can be easily applied. Further, it is possible to easily hold the submucosa 42 by means of the linear portion 23 of the hood main body 17.

At the time of the peripheral incision of the site of lesion 40 and peeling of the submucosa 42, the rinse water, the body fluid and the like entering the inner surface 14 of the hood main body 17 can be removed outside the hood 1 by means of the drain hole 24.

The drain hole 24 also acts as the air-intake opening for aspiration through the treatment tool outlet port 8. Accordingly, when the site of lesion 40 adsorbs to the tip end side opening 10 of the hood main body 17, the excessive aspiration is not performed, the work space on the inner surface 14 of the hood main body 17 is not narrowed by the aspiration of the site of lesion 40, and it is possible to sufficiently aspirate and discharge the water from the treatment tool outlet port 8, so that the eyesight of the endoscope 2 is ensured.

When the inner surface 14 is subjected to the hydrophilic treatment, the rinse water, the body fluid and the like easily flow to the tip end side opening 10 and the drain hole 24, so that the treatment may be performed efficiently and the air can be taken from the drain hole 24. Accordingly, by the synergy effect with the hydrophilic treatment, the water, the body fluid and the like can be discharged from the treatment tool outlet port 8, so that the eyesight of the endoscope 2 can also be ensured.

As described above, by means of the endoscope hood of the present invention, it is possible to allow the endoscope hood to easily get between the mucosa and the muscle layer while the excellent endoscope eyesight is ensured in endoscopic submucosal resection and the like. The tensile force can be thus easily applied for peeling the ablated mucosa from the muscle layer, so that assist such as mucosa dissection and the like can be easily performed.

The present application claims the benefit of the priority of the Japanese Patent Application No. 2009-095467 filed on Apr. 10, 2009, and the entire disclosure thereof is herein incorporated.

The invention claimed is:

1. A cylindrical endoscope hood having both ends open, the endoscope hood being used by mounting on a tip end portion in a longitudinal axis direction of the endoscope, the endoscope including an optical system including at least an observation optical system and a treatment system, the endoscope hood comprising:
an endoscope mounting unit including a base end side opening which is configured to be mounted on the tip end portion of the endoscope; and
a hood main body extending from the endoscope mounting unit to the direction away from the endoscope to a tip end side opening, wherein the tip end side opening has an outer diameter smaller than that of the base end side opening, the outer diameter of the tip end side opening being perpendicular to the longitudinal axis direction of the endoscope,
wherein a cross section in the longitudinal axis direction of the hood main body has an outside surface and an inside surface,
the outside surface including an outer upper ridge line and an outer lower ridge line being opposite to the outer upper ridge line and including a linear portion which is substantially parallel to the longitudinal axis of the endoscope,
the inside surface including an inner upper ridge line located on the back side of the outer upper ridge line and an inner lower ridge line located on the back of the outer lower ridge line,
the upper ridge line continuously tapered off from the endoscope mounting unit or a drain hole to a taper tip end portion, the drain hole being optionally provided on the hood main body, the taper tip end portion being located at a front end of the hood main body, both of the outer upper ridge line and the inner upper ridge line being formed from the endoscope mounting unit or the drain hole to the taper tip end portion,
wherein the inner lower ridge being formed from the endoscope mounting unit to the tip end side opening,
wherein both of the outer upper ridge line and the inner upper ridge line are inclined so as to continuously come closer to a longitudinal axis of the endoscope toward the taper tip end portion and the inner lower ridge line is inclined so as to continuously move away from the longitudinal axis of the endoscope toward the tip end side opening,
wherein a first inclination angle is smaller than a second inclination angle, the first inclination angle being an angle between the inner upper ridge line and the longitudinal axis of the endoscope, the second inclination angle being an angle between the outer upper ridge line and the longitudinal axis of the endoscope,
wherein the tip end side opening is formed at a front end of the hood main body and the tip end side opening faces forward,
when the base end side opening is mounted on the tip end portion of the endoscope, the tip end side opening is located more forward than the tip end portion of the endoscope, and the tip end side opening being arranged so as to surround an extension line of the longitudinal axis direction of the hood main body, and the optical system and the treatment system are located on the inside of the tip end side opening when the tip end portion of the endoscope is viewed in the longitudinal axis direction of the endoscope from a front side of the hood main body through the tip end side opening,
wherein a third inclination angle being an angle between the inner lower ridge line and the longitudinal axis of the endoscope, the third inclination angle being about equal to the first inclination angle.

2. The endoscope hood according to claim 1, wherein the tapered portion has an outer surface inclination angle equal to or more than 5 degrees and equal to or less than 30 degrees.

3. The endoscope hood according to claim 1, wherein the tapered portion has an inner surface inclination angle equal to or more than 3 degrees and equal to or less than 20 degrees.

4. The endoscope hood according to claim 1, wherein the tip end side opening of the hood main body has at least one inclined portion at an angle equal to or more than 5 degrees and equal to or less than 30 degrees with respect to a direction perpendicular to a longitudinal axis.

5. The endoscope hood according to claim 1, wherein the drain hole is substantially oval, the substantially oval drain hole being formed to have large size in a circumferential direction.

6. The endoscope hood according to claim 5, wherein the drain hole has an area equal to or more than 3 square millimeters and equal to or less than 15 square millimeters.

7. The endoscope hood according to claim 1, wherein at least an inner surface of the hood main body is subjected to hydrophilic treatment.

8. The endoscope hood according to claim 1, wherein the inner upper ridge line entirely directly contacts an open space between the tip end side opening and the base end side opening.

9. An endoscope comprising an optical system at least including an observation optical system and a treatment system, the endoscope having a tip end portion in a longitudinal axis direction, the tip end portion being mounted on a cylindrical endoscope hood having both ends open,
- wherein the endoscope hood includes an endoscope mounting unit having a base end side opening which is configured to be mounted on the tip end portion of the endoscope; and
- a hood main body having a tip end side opening extending from the endoscope mounting unit to the direction away from the endoscope to a tip end side opening, wherein the tip end side opening has an outer diameter smaller than that of the base end side opening, the outer diameter being perpendicular to the longitudinal axis direction,
- wherein a cross section in the longitudinal axis direction of the hood main body has an outside surface and an inside surface, the outside surface including an outer upper ridge line, and an outer lower ridge line being opposite to the outer upper ridge line and including a linear portion which is substantially parallel to the longitudinal axis of the endoscope, the inside surface including an inner upper ridge line located on the back side of the outer upper ridge line and an inner lower ridge line located on the back of the outer lower ridge line, the upper ridge line continuously tapered off from the endoscope mounting unit or a drain hole to a taper tip end portion, the drain hole being optionally provided on the hood main body, the taper tip end portion being located at a front end of the hood main body, both of the outer upper ridge line and the inner upper ridge line being formed from the endoscope mounting unit or the drain hole to the taper tip end portion,
- wherein the inner lower ridge being formed from the endoscope mounting unit to the tip end side opening,
- wherein both of the outer upper ridge line and the inner upper ridge line are inclined so as to continuously come closer to a longitudinal axis of the endoscope toward the taper tip end portion and the inner lower ridge line is inclined so as to continuously move away from the longitudinal axis of the endoscope toward the tip end side opening,
- wherein a first inclination angle is smaller than a second inclination angle, the first inclination angle being an angle between the inner upper ridge line and the longitudinal axis of the endoscope, the second inclination angle being an angle between the outer upper ridge line and the longitudinal axis of the endoscope,
- wherein the tip end side opening is formed at a front end of the hood main body and the tip end side opening faces forward,
- wherein the tip end side opening is located more forward than the tip end portion of the endoscope, and the tip end side opening being arranged so as to surround an extension line of the longitudinal axis direction of the hood main body, and
- wherein when the tip end portion of the endoscope is viewed in the longitudinal axis direction from a front side of the hood main body through the tip end side opening, the optical system and the treatment system are located on the inside of the tip end side opening,
- wherein a third inclination angle being an angle between the inner lower ridge line and the longitudinal axis of the endoscope, the third inclination angle being about equal to the first inclination angle.

10. The endoscope according to claim 9, wherein the hood main body has a tapered shape tapering off from the endoscope mounting unit toward the tip end side opening, and when the tip end portion of the endoscope is viewed in the longitudinal axis direction, the observation optical system has a central axis in the longitudinal axis direction, the central axis being arranged at an angle equal to or more than 30 degrees and equal to or less than 60 degrees or equal to or more than −60 degrees and equal to or less than −30 degrees around a center of the base end side opening with respect to an axis passing through an innermost position of the tip end side opening and the center.

* * * * *